United States Patent [19]

Scheffler et al.

[11] Patent Number: 4,618,692

[45] Date of Patent: Oct. 21, 1986

[54] 4-CARBAMOYLOXY-OXAZAPHOSPHO-RINS

[75] Inventors: Gerhard Scheffler; Ulf Niemeyer; Norbert Brock, all of Bielefeld; Jörg Pohl, Halle, all of Fed. Rep. of Germany

[73] Assignee: Asta-Werke Aktiengesellschaft, Bielefeld, Fed. Rep. of Germany

[21] Appl. No.: 579,570

[22] Filed: Feb. 13, 1984

Related U.S. Application Data

[63] Continuation of Ser. No. 299,006, Sep. 3, 1981, abandoned.

[51] Int. Cl.⁴ .............................. C07F 9/24; C07F 9/65
[52] U.S. Cl. ........................................ 558/81; 544/57; 546/22
[58] Field of Search .......................... 260/936; 558/81; 544/57; 546/22

[56] References Cited

FOREIGN PATENT DOCUMENTS 2084154 4/1982 United Kingdom ................ 260/936

*Primary Examiner*—Anton H. Sutto
*Attorney, Agent, or Firm*—Pearne, Gordon, Sessions, McCoy, Granger & Tilberry

[57] ABSTRACT

The present invention relates to new 4-carbamoyloxy-oxazaphosphorins of the general Formula I

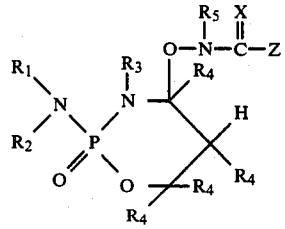

as well as to a method for the treatment of malign tumor diseases in humans using such compounds as active agent.

10 Claims, No Drawings

4-CARBAMOYLOXY-OXAZAPHOSPHORINS

This is a continuation of application Ser. No. 299,006, filed Sept. 3, 1981, now abandoned.

It is known from German Offenlegungsschriften Nos. 2 231 311 and 2 552 135 that the introduction of a hydroperoxy group —OOH into the 4-position of the known cytostatics 2-[bis-(2-chloroethyl)-amino]-2-oxo-tetrahydro-2H-1,3,2-oxazaphosphorin(cyclophosphamide), 3-(2-chloroethylamino)-2-[bis-(2'-chloroethyl)-amino]-2-oxo-tetrahydro-2H-1,3,2-oxazaphosphorin(trofosfamid), 3-(2-chloroethylamino)-2-(2'-chloroethylamino)-2-oxo-tetrahydro-2H-1,3,2-oxazaphosphorin(ifosfamid), 3-(2-chlorethylamino)-2-(2'-methanesulfonylamino)-2-oxo-tetrahydro-2H-1,3,2-oxazaphosphorin(sufosfamid) and other similar cyclophosphamides yield compounds having valuable cytostatic properties. It is therefor an object of the present invention to provide new cyclophosphamide compounds substituted in the 4-position by a further converted hydroxy group which are characterized in particular by a high cytostatic activity and an improved stability.

The new compounds of the present invention represent 4-ureido-oxazaphosphorins of the formula

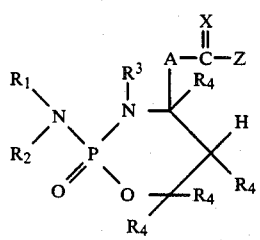

in which A is the group

or the group

Z is the group

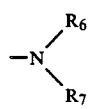

or the group —OR$_7$; X is oxygen or sulphur; R$_1$, R$_2$ and R$_3$, which may be the same or different, represent hydrogen, methyl, ethyl, 2-chloroethyl or 2-methanesulphonyloxyethyl; the groups R$_4$, which may be the same or different, represent hydrogen, methyl or ethyl; R$_5$ and R$_6$, which may be the same or different, represent hydrogen, C$_{1-4}$-alkyl, hydroxy-C$_{1-4}$-alkyl or phenyl provided, however, that R$_5$ cannot be hydrogen when Z is

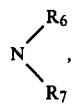

R$_7$ is hydrogen, the carbamoyl group, —OR$_8$ (in which R$_8$ is hydrogen, C$_{1-4}$-alkyl, phenyl or benzyl), straight or branched chain C$_{1-18}$-alkyl (optionally substituted by 1 to 3 substituents which may be the same or different and are selected from the group consisting of hydroxy, halogen, —COOH, —COOR$_9$, —CONH$_2$, —phenyl, benzyloxycarbonyl, —N(R$_9$)$_2$, —$\overset{\oplus}{N}$(R$_9$)$_3$, —OR$_9$, —SR$_9$, —SO—R$_9$, —SO$_2$—R$_9$, —SO$_3$H or —PO(CH$_3$)$_2$, in which R$_9$ represents methyl or ethyl), phenyl-C$_{1-4}$-alkyl (optionally substituted by 1 or 2 carboxy groups in the phenyl and/or alkyl part), allyl, C$_{3-8}$-cycloalkyl, tetrahydrofuranyl, tetrahydropyranyl, phenyl (optionally substituted by one or two C$_{1-4}$-alkyl, C$_{1-2}$-alkoxy, nitro, halogen, trifluormethyl, —SO$_2$NH$_2$, carboxy, benzyloxycarbonyl and/or carb-C$_{1-4}$-alkoxy), benzyl, benzhydryl, naphthyl, fluorenyl, pyridyl, thienyl, benzoyl or C$_{1-4}$-alkanoyl; or R$_5$ and R$_6$ or R$_6$ and R$_7$ together with the atoms to which they are connected form a saturated heterocyclic ring optionally containing an oxygen atom, a C$_{1-4}$-alkyl substituted nitrogen atom or an —S—, —SO— or —SO$_2$— group; or R$_6$ and R$_7$ together with the adjacent nitrogen form an aziridin ring optionally substituted by a cyano or carbamoyl group, and the pharmaceutically useful salts thereof.

Due to their particularly favourable properties and ease of manufacture, the preferred compounds of formula I are those in which Z is

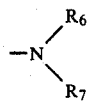

x is oxygen; R$_5$ and R$_6$, which may be the same or different, are hydrogen, methyl or ethyl; and R$_7$ is hydrogen, straight or branched chain C$_{1-18}$-alkyl, phenyl or benzyl.

Particularly preferred compounds are those of the above preferred compounds in which all R$_4$ groups in formula I represent hydrogen atoms.

Another group of preferred compounds are those of formula I in which X is oxygen, R$_1$, R$_2$ and R$_3$ which may be the same or different, represent hydrogen or the 2-chloroethyl group, R$_4$, R$_5$ and R$_6$ represent hydrogen and R$_7$ is hydrogen, benzyl, phenyl (optionally substituted by one or two carboxy groups), C$_{1-4}$-alkyl (optionally substituted by one carboxy group) or phenyl-C$_{1-4}$-alkyl (optionally substituted by one or two carboxy groups in the phenyl and/or alkyl part of the group).

The 4-ureido-oxazaphosphorin compounds wherein A is

in according to the invention, by reacting a compound of formula II

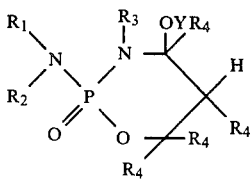

in which $R_1$, $R_2$, $R_3$ and $R_4$ are as defined in formula I and Y is hydrogen, methyl or ethyl, with a compound of formula III

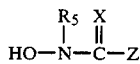

in which Z, $R_5$ and X are as defined in formula I except that $R_5$ may not be hydrogen, in the presence of an inert solvent, optionally with heating or cooling and/or in the presence of an acid catalyst. When $R_5$ is hydrogen and Z is

the 4-ureido-oxazaphosphorin compounds are obtained wherein A in formula I is

in accordance with the invention.

Water, lower alkyl halides such as methylene chloride, lower alkyl ketones such as acetone, diethyl ether, dimethylformamide (DMF), hexamethylphosphoric acid triamide (HMPT) or or similar solvents or mixtures of such solvents are suitable inert solvents for use in the above process. The reaction may be carried out at temperatures in the range from $-35°$ C. to $+50°$ C., that is to say possibly with cooling, at room temperature or with heating. The reaction can be carried out in the presence of an acid catalyst such as an inorganic acid, trichloroacetic acid, trifluoromethanesulphonic acid or a Lewis acid such as $AlCl_3$, $ZnCl_2$ or $TiCl_4$.

Another embodiment of the process to produce the 4-ureido-oxazaphosphorin compounds wherein A is

in formula I, and Z is

(with $R_6$ being hydrogen) and is characterized in that an oxime of formula IV

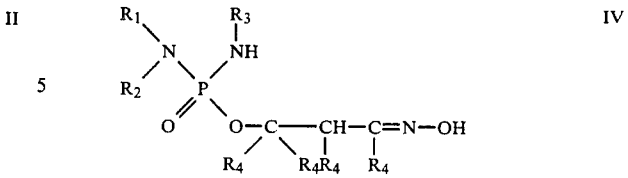

wherein $R_1$ to $R_4$ are as defined in formula I, is subjected to reaction with a compound of formula V

wherein X and $R_7$ are as defined in formula I, in an inert solvent at a temperature ranging from $-70°$ C. to $+50°$ C.

The course of the reaction in both embodiments can be followed by thin layer chromatography. The isolation of thin layer chromatographically uniform substances is achieved by conventional proparation processes for such products, particularly by crystallisation or chromatographic purification.

Confirmation of structure may be effected by melting point, thin layer chromatography, elementary analysis, infra red and/or $^1$H-NMR spectral analysis.

The compounds of formulae II and III used as raw materials in the method according to the invention are largely known and may be used in crystalline form or as a crude product. They can be synthesized in known manner, for example as follows:

4-Hydroxy-oxazaphosphorins are obtained by reduction of the 4-hydroperoxy-derivatives (see for example A. TAKAMIZAWA et al., J.MED.CHEM. 18, 376 (1975)). The 4-methoxy- or 4-ethoxy-oxazaphosphorins may be formed under acid catalysis from the 4-hydroxy derivatives in methanol or ethanol or in inert solvents which contain methanol or ethanol. The hydroxy urea derivatives are produced by the conversion of suitably substituted isocyanates or carbamic acid chlorides with hydroxylamine or N-monosubstituted hydroxylamines.

Racemic cis- and trans-isomers can be produced from the 4-ureido-oxazaphosphorins according to the invention. The cis configuration is 2R, 4R/2S, 4S whilst the trans configuration is 2R, 4S/2S, 4R which correlation is in accordance with the IUPAC nomenclature rules and with the literature concerning corresponding oxazaphosphorin derivatives. The cis- or trans-form can be produced deliberately by selection of the reaction conditions. Pharmacologically, the isomers do not display any significant differences.

The compounds according to the invention possess particularly valuable chemotherapeutic properties. In comparison with the previously known cyclic phosphamides such as cyclophosphamide, trofosfamide, ifosfamide and sufosfamide, they display substantially equal carcinotoxic chemotherapeutic effectiveness on experimental transplant tumours in rats. They have a direct alkylating effect in aqueous solution and have a high cytotoxicity in vitro, unlike the cyclic phosphamides where, for example, cyclophosphamide requires an enzymatic activation and has practically no cytotoxic effect in vitro. The acute toxicity of the compounds according to the invention is considerably lower than that of the known cyclic phosphamides, for example it is about 4 times less than that of the reference substance cyclophosphamide, and thus the therapeutic ratio of the compounds of the invention is considerably improved.

The compounds according to the invention also have clear advantages over the prior art cyclic phosphamides with regard to organotoxic side effects such as leukocyte depression and immunosuppression.

The 4-ureido-oxazaphosphorins according to the present invention are useful in the treatment of malign tumors and similar malign diseases such as leukemia. They are administered in daily dosages in the range of 0.01 to 100 mg. per kg. of body weight. The pharmaceutical preparations used in such therapy are those usual for cyclophosphamide and the other known cytostatic oxazaphosphorins. They may be produced in a usual manner using usual additives, diluents and/or carrier materials.

The compounds of the present invention may be administered to animals in the same manner and against the same disease conditions as those known in connection with the above mentioned cyclic phosphamides. However in view of the lower toxicity of the compounds of the invention they can be used at higher dosage rates and therefore possess a significantly expanded effective therapeutic dosage range. Normally, the compounds of the invention are administered in conventional formulations produced by mixing the compounds with physiologically acceptable vehicles and/or diluents and by conventional routes for example orally or by injection. The production of such formulations and the methods by which they are administered are well known to those skilled in the art.

The compounds according to the present application are useful in the preparation of pharmaceutical products or drugs containing as active agent one or several of such compounds, possible together with other pharmacologically or pharmaceutically active agents. The production of the pharmaceutical preparation is effected in manners known per se using known and usual pharmaceutical auxiliary agents or usual carrier materials or diluents.

Useful as carrier and auxiliary materials are for instance compounds which are described in Ullmanns Encyklopaedie der Technischen Chemie (1953) vol. 4, pgs. 1 to 39; Journal of Pharmaceutical Sciences, (1963), vol. 52, pgs. 918 and following; H. v. Czetsch-Lindenwald, Hilfsstoffe für Pharmazie und angrenzende Gebiete, Pharm. Ind. (1961), vol. 2, pgs. 72 and following; Dr. H. P. Fiedler, Lexikon der Hilfsstoffe für Pharmazie, Kosmetik und angrenzende Gebiete, Cantor KG. Aulendorf (Württemberg) 1971.

Examples are gelatine, natural sugars such as cane sugar or lactose, lecithine, pectin, starch (such as corn starch), alginic acid, tylose, talkum, lycopodium, silicic acid (for instance colloidal silicic acid), cellulose, cellulose derivatives (for instance cellulose ethers, the hydroxy group whereof being partly etherized with lower aliphatic saturated alcohols and/or lower aliphatic saturated oxyalcohols, such as methyloxypropylcellulose), stearates, magnesium and calcium salts of fatty acids having from 12 to 22 C-atoms, in particular of saturated fatty acids (such as stearates), emulgators, oils and fats, in particular plant fats (such as peanut oil, castor oil, olive oil, sesame oil, cottonseed oil, corn oil, wheatgrain oil, sunflower oil, codfish leaver oil, mono-, di- and triglycerides of saturated fatty acids $C_{12}H_{24}O_2$ to $C_{18}H_{36}O_2$ and mixtures thereof), pharmaceutically compatible mono- or polyols and polyglycols such as polyethyleneglycol and derivatives thereof, esters of aliphatic saturated or unsaturated fatty acids (having from 2 to 22, in particular from 10 to 18 carbon atoms) with aliphatic monoalcohols (having from 1 to 20 carbon atoms) or of polyols such as glycols, glycerol, diethyleneglycol, pentaerythritol, sorbitol, mannitol and the like which possibly are etherized; benezylbenzoate, dioxolanes, glycerol formales, tetrahydrofurfuryl alcohol, polyglycol ether with $C_1$–$C_{12}$-alcohols, dimethylacetamide, lactamides, lactates, ethylcarbonates, silicones (in particular dimethylpolysiloxanes having a medium range viscosity), magnesiumcarbonate and the like.

For preparing solutions there are used for instance water or physiologically compatible organic solvents such as ethanol, 1.2-propyleneglycole, polyglycoles and derivatives thereof, dimethylsulfoxide, fatty alcohols, triglycerides, partial esters of glycerol, paraffines and the like.

In the preparation of the pharmaceutical products there may be used usual and known solubilizers or emulgators, for instance: polyvinylpyrrolidone, sorbitane fatty acid esters such as sorbitane trioleate, lecithine, acacia, tragacanth, polyoxyethyl sorbitane monooleate, polyoxyethylized fats, polyoxyethylized oleotriglycerides, linolized oleotriglycerides, polyethyleneoxide-condensation products of fatty alcohols, alkylphenols or fatty acids or 1-methyl-3-(2-hydroxyethyl)-imidazolidon-(2). As above used, polyoxyethylized means that the respective compound contains polyoxyethylene chains with a polymerisation degree generally between 2 to 40 and in particular 10 to 20.

Such polyoxyethylized products may for instance be produced by subjecting the corresponding hydroxy compound (for instance a mono- or diglyceride or unsaturated compound such as containing the unsaturated oleyl group) with ethylene oxide (for instance with 40 moles of ethylene oxide per mole of glyceride).

Examples for oleotriglycerides are olive oil, peanut oil, castor oil, sesame oil, cottonseed oil, corn oil (see for instance Dr. H. P. FIEDLER "Lexikon der Hilfsstoffe für Pharmazie, Kosmetik und angrenzende Gebiete (1971), pgs. 191 to 195).

Furthermore, the pharmaceutical preparations according to the present invention may contain preservatives, stabilysing agents, buffering agents, such as $CaHPO_4$, colloidal aluminum hydroxide, flavoring agents, antioxidants and complex forming agents (such as ethylenediaminotetraacetic acid) and the like. Possibly, the pH is rendered, to about 3 to 7 by means of physiologically compatible acids or buffers in order to stabilize the active agent. An almost neutral or weakly acid pH (up to pH 5) is generally preferred. Useful antioxidants are for instance sodium metabisulfite, ascorbic acid, gallic acid, gallic acid alkylesters, butylhydroxyanisol, nordihydroguajaric acid, tocopheroles as well as combination of tocopheroles and synergistically active agents (agents binding heavy metal cations by complex formation, such as lecithine, ascorbic acid, phosphoric acid). The addition of synergistically active agents considerably increases the antioxidizing activity of tocopheroles.

Useful preservatives are for instance sorbic acid, p-hydroxybenzoic acid esters (such as lower alkyl esters), benzoic acid, sodium benzoate, trichloroisobutyl alcohol, phenol, cresol, benzethonium chloride and formaldehyde derivatives.

The conversion of the compounds according to the present invention into pharmaceutical products occurs with the application of usual galenic principals and usual methods. For instance, the active agent or agents and auxiliary and/or carrier materials are thoroughly mixed (for instance by means of usual mixers), applying generally temperatures between 20° and 80° C., preferably between 20° and 50° C., in particular at room temperature. For further details see: Sucker, Fuchs, Speiser, Pharmazeutische Technologie, Stuttgart (1978).

The compounds according to the present invention and, respectively, the pharmaceutical preparations containing the same are administered on the skin or on mucous membranes or for instance orally, enterally, pulmonally, rectally, by way of the nose, vagina or tongue, intravenously, intraarterially, intracardially, intramuscularly, intraperitoneally, intracutanously, subcutanously, intrapleurally, intrathecally and generally intracaviterally.

In view of its very favourable results it is preferred to combine the active compounds according to the present invention with other active compounds usual in drugs, in particular with uroprotecting agents (for instance and preferably sodium-2-mercapto-ethane sulfonate or the disodium salt of 2.2'-dithiodi-(ethane sulfonic acid), but also with other systemically or regionally detoxifying agents.

The compounds according to the present invention show a good cytostatic and curative activity upon intravenous, intraperitoneal or oral application to rats and mice suffering from various experimental tumors.

For instance, depending upon the dose, a curative activity is achieved with the compounds according to the present invention after administering them intravenously, intraperitoneally or orally in varying dosages one day after intraperitonial implantation of cells of Yoshida-ascites-sarkoma AH 13. For instance, tumor ascites is collected under steril conditions (verified by bacteriological control) from rats having a Yoshida-ascites-sarkoma 5 to 7 days old. The average cell count of the ascites was 2 times $10^5$ cells per $\mu$l. The cell count is brought to $10^8$ cells/ml by the addition of tyrode solution. 0.4 ml thereof ($=4 \times 10^7$ cells) are implanted intraperitoneally to the test animals.

In the untreated control animals the rate at which these tumors start to grow is 95%, the mean mortality time is 8 days (e= ±0.5 d). The compounds to be tested are administered, also intraperitoneally, 3 hours after implantation of the tumors. 6 animals are used in each test group.

The criterion of curative activity is the cure defined as freedom from relapse and metastasis, for 90 days after treatment. After determination of the percent rate of cure the dose with produces cure in 50% of the animals is calculated from the dose activity line by means of probit analysis according to R. Fischer. This DC 50 is the dose at which 50% of the tumor infected animals are cured. This dose for the compounds of the present invention in the above test method upon intraperitoneal administration, is for instance between 0.05 and 30 mg/kg in rats. For instance, with the dose DC 50 the mean survival time against leukemia L1210 in mice can be prolonged for 100%.

For determining the cytotoxic activity in vitro, freshly collected cells of Yoshida ascites sarkoma are incubated for 2 hours at 37° C. with increased concentrations of the compounds to be tested in Ringer solution, as described by Schmähl and Druckrey, Naturwissenschaften, vol. 43 (1956) p. 199. After washing out of the test compound, the transplantability of the tumor cells to untreated test animals is determined. A quantitative value of the cytotoxic activity in vitro can be obtained by determining the concentration EC 50 at which the survival of the transplanted tumor cells in half of the animals is suppressed. With the compounds of the present invention, the above test shows for instance in vitro cytotoxic activity in concentrations ranging from 1 to 100 $\mu$g /ml.

For testing the activity of the compounds of the present invention against leukemia L5222 in rats, the blood of the donar rats of the strain BD IX was withdrawn by cardiopuncture in pentobarbital narcosis (intraperitoneal application). The leukocyte number in the blood varied between 50,000 and 150,000 cells per $\mu$l. the blood is diluted with sterile sodium chloride solution to a leukocyte number of $5 \times 10^3$ cell/$\mu$l. 1 ml. (=$5 \times 10^6$ cells) are implanted intraperitoneally to test animals of the same strain. The rate at which this tumor starts to grow is 100%, the time until death of the test animals varies between 8 and 10 days. 6 animals are used for each test group. The test compounds were administered 5 days after implantation of the leukemia. The criterion of curative effectiveness is the freedom from relapse for 90 days after treatment. After determination of the percent rate of cure, the DC 50 dose can be determined from the dose activity line by means of a probit analysis according to R. FISCHER. This is the dose producing cure in 50% of the test animals. This DC 50 for leukemia L5222 in rats with the compounds according to the present invention upon intraperitoneal administration is for instance in the range of 0.5 to 20 mg/kg of rats.

Furthermore, the compounds according to the present invention have been administered one or several times (4 times) during subsequent days after intraperitoneal implantation of $10^6$ cells of leukemia L1210 of mice at varying dosages and a cytostatic activity was achieved.

The cytostatic activity is the prolongation of the mean survival time of tumor animals, i.e. the dose dependent percent prolongation of the survival time over an uninfested control group. This test method is described for instance by N. Brock, Pharmakologische Grundlagen der Krebs-Chemotherapie in A. Georgii, Verhandlungen der Deutschen Krebsgesellschaft, vol. 1 (1978) pgs. 15 to 42.

This curative and cytostatic activity is comparable with that of the known cytostatics cyclophosphamide and ifosfamide.

The compounds according to the present invention furthermore show a good therapeutic breadth. Furthermore, they have definite advantages over the known cytostatic cyclophosphamide in view of the lower organotoxic side effects such as decrease of the number of leucocytes and immunosuppression. Furthermore, the urotoxicity of the compounds according to the present invention is considerably lower. It can be further avoided by prophylactic administration of a uroprotector, for instance and preferably of sodium-2-mercapto-ethane sulfonate.

The lowest, already curative or cytostatic dose in the above animal tests is for instance
0.01 mg/kg upon oral administration,
0.01 mg/kg upon intraperitoneal administration,
0.01 mg/kg upon intravenous administration.

The general dose range for the curative and cytotatic activity (animal tests as above) is for instance:
0.01–100 mg/kg orally, in particular 0.1–10.0 mg/kg,
0.01–100 mg/kg intraperitoneally, in particular 0.01–10.0 mg/kg, 0.01–100 mg/kg intravenously, in particular 0.1–10.0 mg/kg.

The compounds according to the present invention are useful for the treatment of malign diseases in animals.

The pharmaceutical preparations in general contain between 1 mg and 1 g, preferably between 10 and 300 mg of the active compound or compounds according to the present invention.

The administration may be effected for instance by means of tablets, capsules, pills, dragees, suppositories, ointments, gelees, cremes or in liquid form. Liquid forms of application are for instance oily solutions or solutions in alcohol or water as well as suspensions and emulsions. The preferred form of adiminstration are tablets, containing between 10 and 200 mg of the active compound or solutions containing between 0.1 and 5% of the active compound.

The single dose at which the compounds according to the present invention are administered may be for instance:

(a) between 1 and 100 mg/kg, preferably between 10 and 60 mg/kg for pharmaceutical preprations to be administered orally;
(b) between 1 and 100 mg/kg, preferably between 10 and 60 mg/kg for pharmaceutical preparations for parenteral administration (for instance for intravenous or intramuscular administration);
(c) between 1 and 100 mg/kg, preferably between 10 and 60 mg/kg for pharmaceutical preparations for rectal or vaginal application;
(d) between 1 and 100 mg/kg, preferably between 10 and 60 mg/kg for pharmaceutical preprations for local application upon the skin or upon mucous membranes (for instance in the form of solutions, lotions, emulsions, oiintments or the like).

(The above single dosages refer to the free base the active compound.)

For instance there may be administered 1 to 10 tablets 1 to 3 times per day, each tablet containing 10 to 300 mg of the active compound. Or there may be administered one or several ampoules containing 1 to 10 ml with 10 to 50 mg of the active compound 1 or 2 times per day for intravenous injection. The minimal daily dose for oral admnistration may be for instance 200 mg; the maximum daily dose for oral administration should not be higher than 5000 mg. The compounds may also be administered by continuous intravenous drip over 12 or more hours in particular cases.

For the treatment of dogs and cats the oral single dose in general is between about 10 and 60 mg/kg of body weight. The parenteral dose is approximately between 10 and 60 mg/kg of body weight.

For the treatment of horses and cattle the oral single dose in general is between about 10 and 60 mg/kg.The parental single dose is between about 10 and 60 mg/kg of body weight.

The acute toxicity of the compounds of the present application in mice (expressed by LD 50 mg/kg; test method according to Miller and Tainter, Proc. Soc. Exper. Biol. a. Med., vol. 57 (1944) p. 261) is for instance upon oral administration between 100 and 1000 mg/kg or, respectively above 1000 mg/kg.

The pharmaceutical preparations according to the present invention may be used in therapy, in veterinary therapy or in agriculture alone or admixed with other pharmacologically active agents.

The following examples will further illustrate the preparations of the new compounds of the present invention without however limiting the same thereto.

EXAMPLE 1

1-hydroxy-1-[2-[bis-(2-chloroethyl)-amino]-2-oxo-tetrahydro-2-H-1,3,2-oxazaphosphorin-4-yl]-urea 15 g (54 mmol) of 4-hydroxycyclophosphamide (that is to say 2-[bis-(2-chloroethyl)-amino]-4-hydroxytetrahydro-2H-1,3,2-oxazaphosphorin-2-oxide) and 4.4 g (58 mmol) of hydroxyurea were dissolved in 70 ml of DMF, acidified with trichloroacetic acid (pH 3–4) and left for 20 hours at 0° C. in a refrigerator. The resultant crystal sludge was diluted with 70 ml of ethyl acetate and after 2 hours was drawn off by suction, washed, dried and recrystallized from methanol.

Yield: 11.3 g (62% of the theoretical) in the cis form, m.p. 139°–143° C. (decomposition).

EXAMPLE 2

1-hydroxy-1-[2-[bis-(2-chloroethyl)-amino]-2-oxo-tetrahydro-2H-1,3,2-oxazaphosphorin-4-yl]-urea, cis form 1.1 g (4 mmol) of 4-hydroxycyclophosphamide were dissolved in methanol, treated with a trace of trichloroacetic acid, left to stand over night at −25° C., then methanol was gently drawn off, the residue dissolved in a little methylenechloride, dried and concentrated to 1.2 g of 4-methoxycyclophosphamide (that is to say 2-[bis-(2-chloroethyl)amino]-4-methoxy-tetrahydro-2H-1,3,2-oxazaphosphorin-2-oxide). The 1.2 g of 4-methoxycyclophosphamide and 304 mg of hydroxyurea were dissolved in 3 ml of DMF and kept in a refrigerator at −25° C. for 20 hours. The crystal sludge was diluted with 3 ml of ethyl acetate, drawn off by suction, washed, dried and recrystallized from methanol.

Yield: 670 mg (50% of the theoretical) of the same product as in Example 1.

EXAMPLE 3

1-hydroxy-1-[2-[bis-(2-chloroethyl)-amino]-2-oxo-tetrahydro-2H-1,3,2-oxazaphosphorin-4-yl]-urea, trans form 16 g (58 mmol) of 4-hydroxycyclophosphamide and 5.2 g (68 mmol) of hydroxyurea were dissolved in 160 ml of water, acidified with trichloracetic acid (pH 3–4) and left to stand for 20 hours at 0° C. in a refrigerator. The crystal sludge was then drawn off by suction, washed with water, dried over $P_2O_5$ under high vacuum and recrystallized from methanol/chloroform.

Yield: 12.7 g (65% of the theoretical) of the trans form of the product in Example 1, m.p. 148° C. (decomposition)

EXAMPLE 4

1-hydroxy-1-[3-(2-chloroethyl)-2-[bis-(2'-chloroethyl)-amino]-2-oxo-tetrahydro-2H-1,3,2-oxazaphosphorin-4-yl]-urea 20 g (50 mmol) of 4-hydroxytrofosfamide (that is to say 3-(2-chloroethyl)-2-[bis-(2'-chloroethyl)-amino]-4-hydroxytetrahydro-2H-1,3,2-oxazaphosphorin-2-oxide) and 5.3 g (70 mmol) of hydroxyurea were dissolved in 100 ml of DMF and cooled to −15° C. Then acidification was effected with trichloroacetic acid (pH 3–4) and agitation effected for 5 hours at −15° C. After standing overnight at 0° C., the reaction solution was diluted with twice the amount of water. Then extraction by shaking was effected 4 times each with 300 ml of acetic ester/methanol (10:1), the combined acetic ester phase was washed twice with water, dried over sodium sulphate and doncentrated to 22 g of oil under vacuum. After absorption in ethyl acetate/methanol, 4.2 g (Schmp. 106°–110° C.) crystallized out. The mother liquor was fractionated by column chromatography on silica gel with chloroform/methanol (10:1) and recystallized together with the 1st crystallisate from ethyl acetate/methanol.

Yield: 7.0 g (35% of the theoretical ), m.p. 115°–116° C. (decomposition).

EXAMPLE 5

3-benzyl-1-hydroxy-1-[2-(bis-(2-chloroethyl)-amino)-2-oxo-tetrahydro-2H-1,3,2-oxazaphosphorin-4-yl]-urea 540 mg (3.25 mmol) of 3-benzyl-1-hydroxyurea in 40 ml of acetone and a catalytic amount of trichloroacetic acid were added to 900 mg (3.25 mmol) of 4-hydroxycyclophosphamide in 1 ml of methylenechloride. The mixture was stored overnight at −25° C., the crystals were then drawn off by suction, washed with acetone and ether and recrystallized from ethyl acetate.

Yield: 500 mg (40% of the theoretical), m.p. 122°–123° C. (decomposition).

EXAMPLE 6

3-(o-bromophenyl)-1-hydroxy-1-[2-(bis-(2-chloroethyl)-amino)-2-oxo-tetrahydro-2H-1,3,2-oxazaphosphorin-4-yl]-urea 560 mg (2 mmol) of 4-hydroxycyclophosphamide in 10 ml of acetone were treated with 460 mg of 3-o-bromophenyl-1-hydroxyurea and a catalytic amount of trichloroacetic acid and let to stand at −25° C. After 2 days, the crystals were drawn off by suction and recrystallized from acetone.

Yield: 320 mg (32% of the theoretical), m.p. 110°–111° C. (decomposition).

EXAMPLE 7

N-hydroxy-N-[2-(bis-(2-chloroethyl)-amino)-2-oxo-tetrahydro-2H-1,3,2-oxazaphosphorin-4-yl]-N-morpholinocarbonyl-amine 1.2 g (4.3 mmol) of 4-hydroxycyclophosphamide in 15 ml of acetone were treated with 630 mg (4.3 mmol) of N-hydroxymorpholino-carboxamide and a trace of trichloroacetic acid and stored at −25° C. After 4 days the crystals were drawn off by suction and recrystallized from acetone.

Yield: 780 mg (45% of the theoretical), m.p. 123°–124° C. (decomposition).

EXAMPLES 8-70

Similarly, by starting from corresponding 4-hydroxy-tetrahydro-2H—1,3,2-oxazaphosphorin-2 the 4-ureidooxy derivatives of the following general formula are prepared:

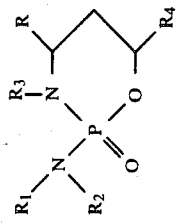

| Example No. | $R_1$ | $R_2$ | $R_3$ | $R_4$ | R | Melting Point or Rf Value (1) |
|---|---|---|---|---|---|---|
| 8  | Cl—CH$_2$CH$_2$— | Cl—CH$_2$CH$_2$— | H— | H— | —N(OH)—CO—NH—CH$_3$ | 106° C. |
| 9  | Cl—CH$_2$CH$_2$— | Cl—CH$_2$CH$_2$— | H— | H— | —N(OH)—CO—NH—CH$_2$—CH$_3$ | 101° C. |
| 10 | Cl—CH$_2$CH$_2$— | Cl—CH$_2$CH$_2$— | H— | H— | —N(OH)—CO—NH—CH(CH$_3$)$_2$ | 99° C. |
| 11 | Cl—CH$_2$CH$_2$— | Cl—CH$_2$CH$_2$— | H— | H— | —N(OH)—CO—NH—(CH$_2$)$_3$—CH$_3$ | 50° C. |
| 12 | Cl—CH$_2$CH$_2$— | Cl—CH$_2$CH$_2$— | H— | H— | —N(OH)—CO—NH—(CH$_2$)$_5$—CH$_3$ | 70–71° C. |
| 13 | Cl—CH$_2$CH$_2$— | Cl—CH$_2$CH$_2$— | H— | H— | —N(OH)—CO—NH—⟨cyclohexyl⟩ | 111° C. |
| 14 | Cl—CH$_2$CH$_2$— | Cl—CH$_2$CH$_2$— | H— | H— | —N(OH)—CO—NH—CH$_2$—CH=CH$_2$ | 65–67° C. |
| 15 | Cl—CH$_2$CH$_2$— | Cl—CH$_2$CH$_2$— | H— | H— | —N(OH)—CO—NH—CH$_2$—C$_6$H$_5$ | 100–101° C. |
| 16 | Cl—CH$_2$CH$_2$— | Cl—CH$_2$CH$_2$— | H— | H— | —N(OH)—CO—NH—CH$_2$—CH$_2$—C$_6$H$_5$ | 113° C. |
| 17 | Cl—CH$_2$CH$_2$— | Cl—CH$_2$CH$_2$— | H— | H— | —N(OH)—CO—NH—CH(CH$_3$)—C$_6$H$_5$ | 130° C. |
| 18 | Cl—CH$_2$CH$_2$— | Cl—CH$_2$CH$_2$— | H— | H— | —N(OH)—CO—NH—CH(C$_6$H$_5$)$_2$ | 98° C. |
| | | | | | —N(OH)—CO—NH—C$_6$H$_5$ | |

-continued
EXAMPLES 8-70
Similarly, by starting from corresponding 4-hydroxy-tetrahydro-2H—1,3,2-oxazaphosphorin-2 the 4-ureidooxy derivatives of the following general formula are prepared:

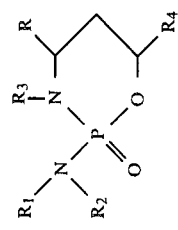

| Example No. | $R_1$ | $R_2$ | $R_3$ | $R_4$ | R | Melting Point or Rf Value (I) |
|---|---|---|---|---|---|---|
| 19 | Cl—CH$_2$CH$_2$— | Cl—CH$_2$CH$_2$— | H— | H— | —N(OH)—CO—NH—(1-naphthyl) | 91–92° C. |
| 20 | Cl—CH$_2$CH$_2$— | Cl—CH$_2$CH$_2$— | H— | H— | —N(OH)—CO—NH—(4-Br-phenyl) | 118–120° C. |
| 21 | Cl—CH$_2$CH$_2$— | Cl—CH$_2$CH$_2$— | H— | H— | —N(OH)—CO—NH—(4-Cl-phenyl) | 118° C. |
| 22 | Cl—CH$_2$CH$_2$— | Cl—CH$_2$CH$_2$— | H— | H— | —N(OH)—CO—NH—(3-Cl-phenyl) | 94° C. |
| 23 | Cl—CH$_2$CH$_2$— | Cl—CH$_2$CH$_2$— | H— | H— | —N(OH)—CO—NH—(4-F-phenyl) | 101° C. |

EXAMPLES 8-70

Similarly, by starting from corresponding 4-hydroxy-tetrahydro-2H—1,3,2-oxazaphosphorin-2 the 4-ureidooxy derivatives of the following general formula are prepared:

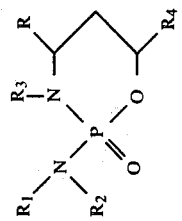

| Example No. | $R_1$ | $R_2$ | $R_3$ | $R_4$ | R | Melting Point or Rf Value (1) |
|---|---|---|---|---|---|---|
| 24 | Cl—CH$_2$CH$_2$— | Cl—CH$_2$CH$_2$— | H— | H— | —N(OH)—CO—NH— (2-F-phenyl) | 116–117° C. |
| 25 | Cl—CH$_2$CH$_2$— | Cl—CH$_2$CH$_2$— | H— | H— | —N(OH)—CO—NH— (4-OCH$_3$-phenyl) | 93–94° C. |
| 26 | Cl—CH$_2$CH$_2$— | Cl—CH$_2$CH$_2$— | H— | H— | —N(OH)—CO—NH— (2-CH$_3$-phenyl) | 101° C. |
| 27 | Cl—CH$_2$CH$_2$— | Cl—CH$_2$CH$_2$— | H— | H— | —N(OH)—CO—NH— (4-NO$_2$-phenyl) | 117–118° C. |
| 28 | Cl—CH$_2$CH$_2$— | Cl—CH$_2$CH$_2$— | H— | H— | —N(OH)—CO—NH— (3-NO$_2$-phenyl) | 111–112° C. |

EXAMPLES 8-70

Similarly, by starting from corresponding 4-hydroxy-tetrahydro-2H—1,3,2-oxazaphosphorin-2 the 4-ureidooxy derivatives of the following general formula are prepared:

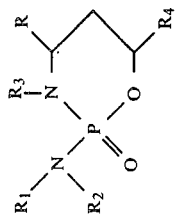

| Example No. | $R_1$ | $R_2$ | $R_3$ | $R_4$ | R | Melting Point or Rf Value (1) |
|---|---|---|---|---|---|---|
| 29 | Cl—CH$_2$CH$_2$— | Cl—CH$_2$CH$_2$— | H— | H— | —N(OH)—CO—NH—(3-CF$_3$-C$_6$H$_4$) | 91–93° C. |
| 30 | Cl—CH$_2$CH$_2$— | Cl—CH$_2$CH$_2$— | H— | H— | —N(OH)—CO—NH—(3,4-Cl$_2$-C$_6$H$_3$) | 107° C. |
| 31 | Cl—CH$_2$CH$_2$— | Cl—CH$_2$CH$_2$— | H— | H— | —N(OH)—CO—NH—(CH$_2$)$_3$—Br | 48–50° C. |
| 32 | Cl—CH$_2$CH$_2$— | Cl—CH$_2$CH$_2$— | H— | H— | —N(OH)—CO—NH—CH$_2$—CH$_2$—Cl | 98° C. |
| 33 | Cl—CH$_2$CH$_2$— | Cl—CH$_2$CH$_2$— | H— | H— | —N(OH)—CO—NH—CH(CH$_3$)—CO$_2$C$_2$H$_5$ | 102–103° C. |
| 34 | Cl—CH$_2$CH$_2$— | Cl—CH$_2$CH$_2$— | H— | H— | —N(OH)—CO—NH—CH$_2$—CH$_2$—OH | 0.35 |
| 35 | Cl—CH$_2$CH$_2$— | Cl—CH$_2$CH$_2$— | H— | H— | —N(OH)—CO—NH—CH$_2$—PO(CH$_3$)$_2$ | 110–113° C. |
| 36 | Cl—CH$_2$CH$_2$— | Cl—CH$_2$CH$_2$— | H— | H— | —N(OH)—CO—NH—CH$_2$—CO$_2$C$_2$H$_5$ | 106° C. |
| 37 | Cl—CH$_2$CH$_2$— | Cl—CH$_2$CH$_2$— | H— | H— | —N(OH)—CO—NH—C$_6$H$_5$ (benzoyl) | 125° C. |
| 38 | Cl—CH$_2$CH$_2$— | Cl—CH$_2$CH$_2$—Cl | H— | H— | —N(OH)—CO—N(CH$_3$)—C$_6$H$_5$ | 0.65 |

-continued
EXAMPLES 8–70
Similarly, by starting from corresponding 4-hydroxy-tetrahydro-2H—1,3,2-oxazaphosphorin-2 the 4-ureidooxy derivatives of the following general formula are prepared:

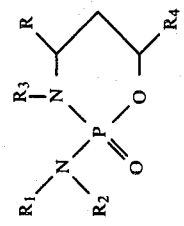

| Example No. | R₁ | R₂ | R₃ | R₄ | R | Melting Point or Rf Value (1) |
|---|---|---|---|---|---|---|
| 39 | Cl—CH₂CH₂— | Cl—CH₂CH₂— | H— | H— | —O—N(CH₃)—CO—NH—C₆H₅ | 125–126° C. |
| 40 | Cl—CH₂CH₂— | Cl—CH₂CH₂— | H— | H— | —O—N(CH₃)—CO—N(CH₃)—C₆H₅ | 0.57 |
| 41 | Cl—CH₂CH₂— | Cl—CH₂CH₂— | H— | H— | —N(OH)—CO—N(thiomorpholine) | 119–121° C. |
| 42 | Cl—CH₂CH₂— | Cl—CH₂CH₂— | H— | H— | —N(OH)—CO—N(C₂H₅)₂ | 92° C. |
| 43 | Cl—CH₂CH₂— | Cl—CH₂CH₂— | H— | H— | —N(OH)—CO—N(CH₃)₂ | 96–98° C. |
| 44 | Cl—CH₂CH₂— | Cl—CH₂CH₂— | H— | H— | —O—N(CH₃)—CO—NH₂ | 115–117° C. |
| 45 | Cl—CH₂CH₂— | Cl—CH₂CH₂— | H— | H— | —O—N(C₂H₅)—CO—NH₂ | 0.51 |
| 46 | Cl—CH₂CH₂— | Cl—CH₂CH₂— | H— | H— | —O—N(CH₃)—CO—NH—CH₃ | 125–127° C. |
| 47 | Cl—CH₂CH₂— | Cl—CH₂CH₂— | H— | H— | —N(OH)—CO—N(CH₃)—(CH₂)₅—CH₃ | 0.63 |
| 48 | Cl—CH₂CH₂— | Cl—CH₂CH₂— | H— | H— | —O—N(C₂H₅)—CO—NH—CH₃ | 112° C. |
| 49 | Cl—CH₂CH₂— | Cl—CH₂CH₂— | H— | H— | —O—N(CH₃)—CO—NH—C₂H₅ | 0.60 |
| 50 | Cl—CH₂CH₂— | Cl—CH₂CH₂— | H— | H— | —O—N(C₂H₅)CO—N(C₂H₅)₂ | 0.61 |
| 51 | Cl—CH₂CH₂— | Cl—CH₂CH₂— | H— | H— | —N(OH)—CS—NH—CH₂—C₆H₅ | 118° C. |

EXAMPLES 8-70

Similarly, by starting from corresponding 4-hydroxy-tetrahydro-2H—1,3,2-oxazaphosphorin-2 the 4-ureidooxy derivatives of the following general formula are prepared:

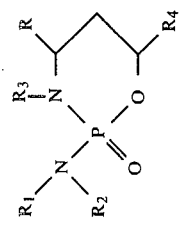

| Example No. | $R_1$ | $R_2$ | $R_3$ | $R_4$ | R | Melting Point or Rf Value (1) |
|---|---|---|---|---|---|---|
| 52 | Cl—CH$_2$CH$_2$— | Cl—CH$_2$CH$_2$— | H— | H— | —N(OH)—CS—NH— (cyclohexyl) | 0.72 |
| 53 | Cl—CH$_2$CH$_2$— | H— | Cl—CH$_2$CH$_2$— | H— | —N(OH)—CO—NH$_2$ | 134° C. |
| 54 | Cl—CH$_2$CH$_2$— | CH$_3$— | Cl—CH$_2$CH$_2$— | H— | —N(OH)—CO—NH$_2$ | 144° C. |
| 55 | CH$_3$SO$_3$—CH$_2$CH$_2$— | CH$_3$— | Cl—CH$_2$CH$_2$— | H— | —N(OH)—CO—NH$_2$ | 114–115° C. |
| 56 | Cl—CH$_2$CH$_2$— | H— | CH$_3$SO$_3$—CH$_2$CH$_2$— | H— | —N(OH)—CO—NH$_2$ | 0.34 |
| 57 | CH$_3$SO$_3$—CH$_2$CH$_2$— | H— | Cl—CH$_2$CH$_2$— | H— | —N(OH)—CO—NH$_2$ | 0.29 |
| 58 | Cl—CH$_2$CH$_2$— | Cl—CH$_2$CH$_2$— | H— | CH$_3$— | —N(OH)—CO—NH$_2$ | 136–138° C. |
| 59 | Cl—CH$_2$CH$_2$— | Cl—CH$_2$CH$_2$— | H— | H— | —N(OH)—CO—NH—C$_{14}$H$_{29n}$ | 0.64 |
| 60 | Cl—CH$_2$CH$_2$— | Cl—CH$_2$CH$_2$— | H— | H— | —N(OH)—CS—NH— (phenyl) | 0.67 |
| 61 | Cl—CH$_2$CH$_2$— | Cl—CH$_2$CH$_2$— | H— | H— | —N(OH)—CO—NH—CO—NH$_2$ | 141° C. |
| 62 | Cl—CH$_2$CH$_2$— | Cl—CH$_2$CH$_2$— | H— | H— | —N(OH)—CO—(piperidinyl) | 109° C. |
| 63 | Cl—CH$_2$CH$_2$— | Cl—CH$_2$CH$_2$— | H— | CH$_3$— | —N(OH)—CO—NH—CH$_2$—(phenyl) | 110–112° C. |
| 64 | Cl—CH$_2$CH$_2$— | Cl—CH$_2$CH$_2$— | H— | H— | —N(OH)—CO—NH—OH | 110–113° C. |

EXAMPLES 8-70

Similarly, by starting from corresponding 4-hydroxy-tetrahydro-2H—1,3,2-oxazaphosphorin-2 the 4-ureidooxy derivatives of the following general formula are prepared:

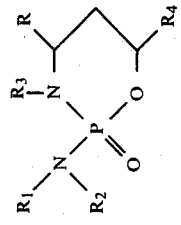

| Example No. | $R_1$ | $R_2$ | $R_3$ | $R_4$ | R | Melting Point or Rf Value (1) |
|---|---|---|---|---|---|---|
| 65 | Cl—CH$_2$CH$_2$— | Cl—CH$_2$CH$_2$— | H— | H— | —N(OH)—CO—NH—⌬—SO$_2$NH$_2$ | 131° C. |
| 66 | Cl—CH$_2$CH$_2$— | Cl—CH$_2$CH$_2$— | H— | H— | —N(OH)—CO—NH—(fluorene) | 114° C. |
| 67 | Cl—CH$_2$CH$_2$— | Cl—CH$_2$CH$_2$— | H— | H— | —N(OH)—CO—NH—(fluorenone) | 133° C. |
| 68 | Cl—CH$_2$CH$_2$— | Cl—CH$_2$CH$_2$— | H— | H— | —N(OH)—CO—NH—CH$_2$—CO$_2$—CH$_2$—⌬ | 119° C. |
| 69 | Cl—CH$_2$CH$_2$— | Cl—CH$_2$CH$_2$— | H— | H— | —N(OH)—CO—NH—CH$_2$—COOH × NH$_2$—(cyclohexyl) | 106–108° C. |
| 70 | Cl—CH$_2$CH$_2$— | Cl—CH$_2$CH$_2$— | H— | H— | —N(OH)—CO—NH—(pyridyl) | 83–85° C. |

(1) The melting points were not corrected. The oily compounds were distinguished by their RF value using thin layer chromatography on silica gel with chloroform/methanol (5:1). Further distinguishing characteristics were determined as with the crystalline compounds.

EXAMPLE 71

Ethyl-2-[bis-(2-chloroethyl)-amino]-2-oxo-tetrahydro-2H-1,3,2-oxazaphosphorin-4-yl-oxy-carbamate 550 mg (2 mmol) of 4-hydroxycyclophosphamide and 210 mg (2 mmol) of ethylhydroxycarbamate (hydroxyurethane) are dissolved in 5 ml of dry methylenechloride free of alcohol. A catalytic amount of trichloroacetic acid and molecular sieve 4 A are added thereto. The reaction mixture is allowed to stand at −25° C. for 3 days. Thereafter, the molecular sieve is separated and washed once with a diluted solution of NaHCO$_3$. The methylenechloride phase is dried over sodium sulfate and part of the solvent is evaporated in a vacuum and thereafter diluted with ether. After standing for 20 hours at −25° C., the separated crystals are filtered off, washed and dried.

Yield: 290 mg (40% of the theoretical) m.p. 96° C.

EXAMPLE 72

Benzyl-2-[bis-(2-chloroethyl)-amino]-2-oxo-tetrahydro-2H-1,3,2-oxazaphosphorin-4-yl-oxy-carbamate 750 mg (2.7 mmol) of 4-hydroxycyclophosphamide and 450 mg (2.7 mmol) of benzyl-hydroxycarbamate are dissolved in 6 ml of methylene chloride free of alcohol. A small amount of trichloroacetic acid is added thereto and the solution is allowed to stand at −25° C. in a refrigerator for 3 days. The resulting solution is filtered off, the mother liquor is diluted with 5 ml of chloroform, then is diluted with water and thereafter is washed with a dilute solution of NaHCO$_3$ and with water. The washed solution is dried over sodium sulfate and is evaporated in a vacuum. The oily residue thereafter is recrystallized from acetic acid ethyl ester containing a small amount of methanol.

Yield: 680 mg (59% of the theoretical) m.p. 112°–114° C.

EXAMPLE 73

{3-hydroxy-[2-(bis-(2-chloroethyl)-amino)-2-oxo-tetrahydro-2H-1,3,2-oxazaphosphorin-4-yl]-ureido}-acetic acid, cyclohexylamine salt (a) 3-hydroxy-ureido-acetic acid 56.5 g (0.28 mole) of glycine benzylester-hydrochloride are suspended in 300 ml of toluene. Dry gaseous phosgene are introduced for 2 hours with stirring while the reaction mixture is heated on an oil bath heated to 140° C. The reaction mixture thereafter is evaporated in a vacuum and the residue of crude benzyl-isocyanatoacetate is destilled in a high vacuum.

Yield: 51 g (95% of the theoretical). B.p.$_{0.05}$: 100°–102° C.

A solution of 6.6 g (0.2 mole) of hydroxylamine in 200 ml of dioxane is added to a solution of 28.7 g (0.15 mole) of benzyl-isocyanato-acetate in 50 ml of dioxane dropwise with stirring and temporary cooling. Stirring is continued for another hour at room temperature. A reaction mixture thereafter is evaporated in a vacuum. The resulting residue of crude benzyl-3-hydroxy-ureido-acetate is recrystallized from ethyl acetate.

Yield: 28.1 g (83.6% of the theoretical) m.p.: 113°–120° C.

5 g of palladium on activated charcoal are added to a solution of 22.4 g (0.1 mole) of benzyl-3-hydroxy-ureido-acetate in 300 ml of methanol. Hydrogen is introduced with shaking. After about 20 minutes the hydrogen uptake is finished. The catalyst is filtered off with suction and the filtrate is evaporated in a vacuum. The solid residue of crude 3-hydroxy-ureido-acetic acid is recrystallized from dioxane.

Yield: 9.8 g (73% of the theoretical) m.p. 135° C.

(b) 6.1 g (2 mmol) of 4-hydroxycyclophosphamide are added to a solution of 2.4 g (18 mmol) of 3-hydroxy-ureido-acetic acid in 10 ml of water and 25 ml of acetone. The reaction mixture is allowed to stand over night at −25° C. Thereafter, 25 ml of acetone and a solution of 1.8 g (18 mmol) of cyclohexylamine in 10 ml of acetone are added thereto. After standing for 2 hours, the precipitate is filtered off with suction and is recrystallized from acetone containing a small amount of methanol.

Yield: 3.1 g (44% of the theoretical) m.p. 107°–108° C.

EXAMPLE 74

3-[N,N-(bis-(2-chloroethyl)-diamino)-phosphinyl-oxy]-propionaldehyde-oxime (aldophosphamide-oxime)

4.0 g (13.7 mmol) of 4-hydroperoxycyclophosphamide are suspended in 50 ml of water with ice-cooling. 500 mg Na$_2$S$_2$O$_3$×5H$_2$O are added thereto. During the stirring at 5° to 10° C. the pH is controlled with a pH-measuring device and is kept between pH 4.5 and 5.5 by the addition of 2nH$_2$SO$_4$. A concentrated solution of sodium thiosulfate is added dropwise thereto until there is no longer observed a continues increase of the pH of the reaction mixture. Stirring is continued for half an hour about 10° C. and an aqueous solution of 950 mg of hydroxylamine-hydrochloride is added dropwise keeping the pH at 5 by the addition of 2n-NaOH. The resulting reaction mixture is allowed to stand overnight in a cooling box at 5° C. Thereafter, the reaction mixture is extracted four times with 50 ml ethyl acetate each and the organic extractes are dried over sodium sulphate and evaporated in a vacuum at 30° C. The residue is dissolved in methylene chloride and the separated crystals are filtered off after one day.

Yield: 3.4 g (85% of the theoretical) m.p.: 79°–81° C.

EXAMPLE 75

3-p-bromophenyl-1-hydroxy-1-[2-(bis-(2-chloroethyl)-amino)-2-oxo-tetrahydro-2H-1,3,2-oxazaphosphorin-4-yl]-urea 4 g (20 mole) of p-bromophenylisocyanate in 40 ml of acetone are added to 5.8 g (20 mmole) of aldophosphamideoxime in 60 ml of acetone. The reaction mixture is stirred with cooling for 5 hours. After standing for 2 hours, the separated crystals are filtered off and dried in a vacuum in a rotation evaporator at 40° C. and are recrystallized in methanol.

Yield: 8.1 g (82.8% of the theoretical) m.p.: 118°–120° C.

EXAMPLE 76

3-m-trifluoromethylphenyl-1-hydroxy1-[2-(bis-(2-chloroethyl)-amino)-2-oxo-tetrahydro-2H-1,3,2-oxazaphosphorin-4-yl]-urea 4.7 g (25 mmole) of m-trifluoromethyl phenylisocyanate dissolved in 40 ml of acetone are added to 7.3 g (25 mmole) of aldophosphamide-oxime in 80 ml of acetone. The reaction mixture is stirred for 3 hours at 0° C. and is allowed to stand overnight in a cooling box at −25° C. Thereafter, 150 ml of petrolether are added thereto and the mixture is allowed to stand for another night in the cooling box at −25° C. The resulting crystals are filtered off, dried at 30° C. and are recrystallized from isopropanol.

Yield: 9.2 g (76.8% of the theoretical) m.p.: 91°–93° C.

EXAMPLE 77

3-cyclohexyl-1-hydroxy-1-[2-(bis(2-chloroethyl)-amino)-2-oxo-tetrahydro-2H-1,3,2-oxazaphosphorin-4-yl]-urea 5 g (18 mmole) of aldophosphamide-oxime and 2.2 g cyclohexylisocyanate are separately dissolved in 10 ml of acetone and the solutions are admixed at 0° C. after standing for 2 hours, the resulting crystals are filtered off with suction and are recrystallized from acetone/ether.

Yield: 4.2 g (56% of the theoretical) m.p.: 113° C.

EXAMPLE 78

3-ethyl-1-hydroxy-1-[2-(bis-(2-chloroethyl)-amino)-2-oxo-tetrahydro-2H-1,3,2-oxazaphosphorin-4-yl]-urea 5 g (18 mmole) of aldophosphamide-oxime and 1.2 g ethylisocyanate are separately dissolved in 15 ml of acetone each. The solutions are admixed at about 0° C. After standing for 5 hours the separated crystals are filtered off with suction and washed with acetone/ether.

Yield: 3.5 g (54% of the theoretical) m.p.: 101° C.

EXAMPLE 79

3-(fluorene-2-yl-1-hydroxy-1-[2-(bis-(2-chloroethyl)-amino)-2-oxo-tetrahydro-2H-1,3,2-oxazaphosphorin-4-yl]-urea 2.1 g (10 mmole) of fluorenyl-2-isocyanate dissolved in 20 ml of acetone are added to 2.9 g (10 mmole) of aldophosphamide-oxime in 30 ml of acetone at 0° C. The separated crystals were filtered off on the next day, are dried in a vacuum at 60° C. and are recrystallized from isopropanol/methanol.

Yield: 2.5 g (50.1% of the theoretical) m.p.: 114° C.

EXAMPLE 80

3-benzoyl-2-hydroxy-1-[2-(bis-(2-chloroethyl)-amino)-2-oxo-tetrahydro-2H-1,3,2-oxazaphosphorin-4-yl]-urea 2.9 g (20 mmole) of benzoylisocyanate dissolved in 40 ml of acetone are added to 5.8 g (20 mmole) of aldophosphamideoxime in 60 ml of acetone. A reaction mixture is stirred for 5 hours under a nitrogen atmosphere with cooling in an ice bath. The separated solid material is filtered off with suction, is dried in a rotating evaporator at 30° C. and is recrystallized from methanol.

Yield: 2.4 g (27.3% of the theoretical) m.p.: 124°–125° C.

EXAMPLE 81

3-p-nitrophenyl-1-hydroxy-1-[2-(bis-(2-chloroethyl)-amino-2-oxo-tetrahydro-2H-1,3,2-oxazaphosphorin-4-yl]-urea 3.3 g (20 mmole) of p-nitrophenylisocyanate dissolved in 40 ml of acetone are added to 5.8 g (20 mmole) of aldophosphamide-oxime in 60 ml of acetone. After standing for 2 hours the separated solid material is filtered off with suction, is dried in a rotating evaporator at 40° C. and is recrystallized from DMF/ethanol.

Yield: 6.7 g 73.5% of the theoretical) m.p.: 117°–118° C.

EXAMPLE 82

Tablet coated with a coating resistant against stomache juices 100 g of the compound of Example 5 together with 7.0 g of Aerosil (i.e. finely devided amorphous silicic acid) are passed through a sieve and are thoroughly mixed. To this mixture there are added 76.0 g of Avicel PH 105 (i.e. micro crystalline cellulose product of FMC), 10 g of corn starch and 7.0 of stearic acid. This mixture is mixed until reaching a homogenous distribution of all components. The mixture is pressed in usual manner to kernels each weighing 200 mg containing 100 mg of the active compound.

The kernels are coated with a usual stomache juice resistant coating, for instance from suitable cellulose derivatives or from a fully synthetic coating from an organic solution or aqueous dispersion which may contain usual plasticizers, dyestuffs, sweeteners or defoamers.

EXAMPLE 83

Gelatine capsule coated with a stomache resistant coating 250 g of the compound of Example 5 together with 7.5 g of Aerosil are passed through a sieve and thoroughly mixed. 40 g of lactose and 2.5 g of magnesium stearate are added to this mixture which is mixed until reaching a homogenous distribution of its components.

This product is filled into gelatine capsules each capsule containing a single dose of 300 mg of the active compound.

The capsules are closed and are coated as described in Example 82.

What we claim is:

1. A 4-ureido-oxazaphosphorin of the general formula I

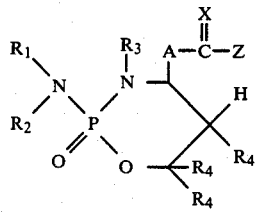

in which A is the group

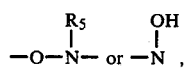

Z is the group

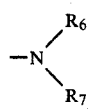

or the group —OR$_7$; X is oxygen or sulphur; R$_1$ is 2-chloroethyl or 2-methanesulphonyloxyethyl; R$_2$ is hydrogen, methyl, ethyl or 2-chloroethyl; R$_3$ is hydrogen, methyl, ethyl, 2-chloroethyl or 2-methanesulphonyloxyethyl; R$_4$ is hydrogen or methyl; R$_5$ is hydrogen or $C_{1-4}$-alkyl; $R_6$ is hydrogen or $C_{1-4}$-alkyl; $R_7$ when in the secondary amino group is hydrogen, hydroxy, the carbamoyl group, $C_{1-4}$-alkyl, allyl, cyclohexyl, phenyl (optionally substituted by one or two of halogen, $C_{1-4}$-alkyl, $C_{1-4}$-alkoxy, trifluoromethyl, nitro or sulfamoyl), benzyl, naphthyl, fluorenyl, 9-oxofluorenyl, benzoyl, $C_{1-4}$-alkyl substituted by 1 to 3 substituents which may be the same or different and are selected from the group consisting of hydroxy, halogen, —COOH, —COOR$_8$, phenyl, benzyloxycarbonyl, and —PO(CH$_3$)$_2$, in which $R_8$ is methyl or ethyl; the total group

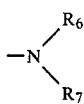

representing the morpholino ring or a saturated heterocyclic ring having from 4 to 6 carbon atoms and a nitrogen atom; $R_7$ when in the ether group is a $C_{1-4}$-alkyl possibly substituted by phenyl; and the pharmaceutically useful salts thereof.

2. A 4-carbamoyloxy-oxazaphosphorin as claimed in claim 1, in which Z is

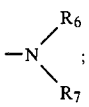

X is oxygen; $R_5$ and $R_6$, which may be the same or different, are hydrogen, methyl or ethyl; and $R_7$ is hydrogen, straight or branch chained $C_{1-18}$-alkyl, phenyl or benzyl.

3. A 4-carbamoyloxy-oxazaphosphorin as claimed in claim 2, in which all $R_4$ Groups in formula I are hydrogen atoms.

4. A 4-carbamoyloxy-oxazaphosphorin as claimed in claim 1, in which X is oxygen; $R_1$, $R_2$ and $R_3$ which may the same or different, are hydrogen or 2-chloroethyl; $R_4$, $R_5$ and $R_6$ are hydrogen and $R_7$ is hydrogen, benzyl, phenyl (optionally substituted by 1 or 2 carboxy group), $C_{1-4}$-alkyl (optionally substituted by 1 carboxy group) or phenyl-$C_{1-4}$-alkyl (optionally substituted by 1 or 2 carboxy groups in the phenyl and/or alkyl part of the group).

5. A 4-ureido-oxazaphosphorin of the general formula I

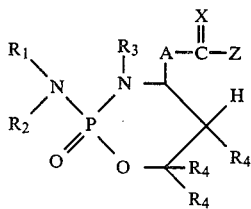

in which A is the group

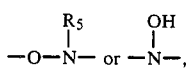

Z is

X is oxygen; $R_1$, $R_2$ and $R_3$, which may be the same or different, represent hydrogen, methyl, ethyl, 2-chloroethyl or 2-methanesulphonyloxyethyl; the groups $R_4$, which may be the same or different, represent hydrogen, methyl or ethyl; $R_5$ and $R_6$, which may be the same or different, are hydrogen, methyl or ethyl; $R_7$ is hydrogen, straight or branch chained $C_{1-18}$-alkyl, phenyl or benzyl (optionally substituted by 1 or 2 carboxy groups); and the pharmaceutically useful salts thereof.

6. A 4-ureido-oxazaphosphorin of the general formula I

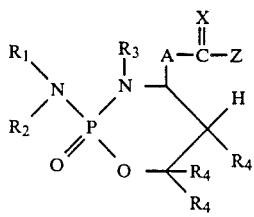

in which A is

Z is

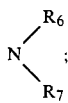

X is oxygen; $R_1$, $R_2$ and $R_3$, which may be the same or different, are hydrogen or 2-chloroethyl; $R_4$, and $R_6$ are hydrogen and $R_7$ is hydrogen, benzyl, phenyl (optionally substituted by 1 or 2 carboxy groups), $C_{1-4}$-alkyl (optionally substituted by 1 carboxy group) or phenyl-$C_{1-4}$-alkyl (optionally substituted by 1 or 2 carboxy groups in the phenyl and/or alkyl part of the group); and the pharmaceutically useful salts thereof.

7. A 4-ureido-oxazaphosphorin of the general formula I

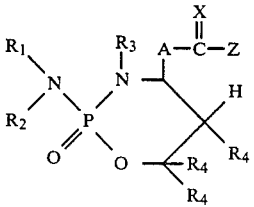

in which A is

Z is

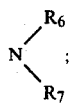
X is oxygen, $R_1$ and $R_2$ are 2-chloroethyl; $R_3$, $R_4$, and $R_6$ are hydrogen; $R_7$ is hydrogen, carboxylic acid, or acetic acid; and the pharmaceutically useful salts thereof.
8. The composition of claim 7, wherein $R_7$ is acetic acid.
9. The sodium salt of the composition of claim 8.
10. The cyclohexylamine salt of the composition of claim 8.
* * * * *